United States Patent [19]

Hagen et al.

[11] 4,248,961

[45] Feb. 3, 1981

[54] MATERIAL FOR COLOR PHOTOGRAPHY

[75] Inventors: Remon Hagen, Chemin Forêt; Mario Fryberg, Praroman-le-Mouret, both of Switzerland

[73] Assignee: Ciba-Geigy G, Basel, Switzerland

[21] Appl. No.: 35,362

[22] Filed: May 2, 1979

Related U.S. Application Data

[63] Continuation-in-part of Ser. No. 859,499, Dec. 9, 1977, abandoned.

[30] Foreign Application Priority Data

Dec. 24, 1976 [CH] Switzerland ............. 16310/76

[51] Int. Cl.$^3$ ............. G03C 7/00; G03C 1/40
[52] U.S. Cl. ............. 430/381; 430/388; 430/389; 430/548; 430/556; 430/557; 430/558
[58] Field of Search ............. 430/381, 389, 548, 557, 430/558, 556

[56] References Cited

U.S. PATENT DOCUMENTS

| | | | |
|---|---|---|---|
| 2,319,426 | 5/1943 | Middleton et al. | 430/381 |
| 2,376,679 | 5/1945 | Frohlich et al. | 430/548 |
| 3,077,403 | 2/1963 | Trucker | 430/548 |
| 3,778,277 | 12/1973 | Fujiwhara et al. | 430/548 |
| 3,960,570 | 6/1976 | Oishi et al. | 430/557 |
| 3,990,896 | 11/1976 | Arai et al. | 430/557 |

FOREIGN PATENT DOCUMENTS 2264308 10/1975 France .
1421123 1/1976 United Kingdom .

OTHER PUBLICATIONS

Research Disclosure 11030, June, 1973.

*Primary Examiner*—J. Travis Brown
*Attorney, Agent, or Firm*—Sprung, Felfe, Horn, Lynch & Kramer

[57] ABSTRACT

Light-sensitive recording material for color photography is provided which contains, in at least one silver halide emulsion layer, a yellow coupler of the formula

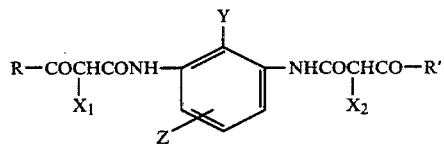

in which R and R' are alkyl, cycloalkyl or aryl and $X_1$ and $X_2$ are radicals which are detachable during the coupling reaction, Y is halogen, alkyl, alkoxy, alkylmercapto, —CN, —COOH, carbalkoxy, —NH$_2$, —NHR$_1$, —NR$_1$R$_2$ or —NHCOR$_1$, in which R$_1$ and R$_2$ are alkyl or phenyl, Z is alkyl having 5 to 40 carbon atoms, alkoxy having 5 to 40 carbon atoms, cycloalkoxy having 5 to 12 carbon atoms or aralkyl; alkoxyalkyl, alkoxycycloalkyl, cycloalkoxyalkyl, optionally substituted phenoxyalkyl, alkylamino- and dialkylamino-alkyl, optionally substituted arylamino- and diarylamino-alkyl, alkylmercaptoalkyl or optionally substituted arylmercaptoalkyl, in which radicals the sum of the carbon atoms in each case is 6 to 40; or —COOR$_3$, —COR$_3$, —NR$_3$R$_4$, —CONR$_3$R$_4$, —NR$_4$COR$_3$, —SO$_2$R$_3$, —SO$_2$NR$_3$R$_4$ or —NR$_4$SO$_2$R$_3$, R$_3$ is optionally substituted alkyl having 1 to 40 carbon atoms, optionally substituted cycloalkyl having 5 to 12 carbon atoms or optionally substituted phenyl and R$_4$ is hydrogen or alkyl having 1 to 12 carbon atoms.

The couplers used according to the invention have a high coupling reactivity towards the oxidation product of the aromatic primary amine (developer), so that the developing of the silver halide emulsion proceeds rapidly.

Furthermore, an adequate color density is achieved, although the molar amount of coupler employed can be markedly reduced compared with that of known couplers.

13 Claims, No Drawings

MATERIAL FOR COLOR PHOTOGRAPHY

This is a continuation-in-part of our copending application Ser. No. 859,499, filed Dec. 9, 1977, now abandoned.

In order to produce coloured photographic images, exposed silver halide emulsion layers which at the same time contain colour couplers are, as is known, developed with a developing agent which contains aromatic primary amino groups. The oxidised developing agent reacts with the colour coupler with the formation of an image dye, the amount of this dye being dependent on the amount of silver developed.

In general, a light-sensitive photographic multi-layer material which consists of a red-sensitive layer, which contains the cyan coupler, a green-sensitive layer, which contains the magenta coupler, and a blue-sensitive layer, which, in turn, contains the yellow coupler, is used. On colour development, the corresponding dyes, which are cyan, magenta and yellow in colour, then form.

Usually, phenols or α-naphthols are employed as cyan couplers, pyrazolones are employed as magenta couplers and acylacetylamides are employed as yellow couplers. The dyes formed after development are then indophenols, indamines or azomethines.

A structural characteristic of the conventional yellow couplers is an active methylene group, it being possible, in some cases, for one hydrogen atom to be replaced by a group which is detachable during the coupling reaction. In the former case, the couplers are termed four-equivalent couplers since four equivalents of silver halide are required in order to form the image dye. In the second case, only two equivalents of silver halide are used to produce the corresponding image dye (two-equivalent couplers). These known couplers result in image dyes which in each case contain a chromogenic grouping (azomethine grouping) and a ballast group. Although the ballast groups are important inasmuch as they are responsible, for example, on the one hand for the solubility of the coupler and on the other hand also for the resistance of the dyes to diffusion, they can, however, also have an adverse influence (for example as a result of undesired light absorption) on the photographic properties of the recording material for colour photography; moreover, they make no contribution towards increasing the colour yield of the image dye to be formed. In order to overcome these disadvantages either the size of the ballast groups can be reduced (which, however, because of the demands made on these groups hardly promises success) or the number of the chromogenic groupings per molecule is increased, i.e. the 1:1 ratio (chromogenic group: ballast group) is changed to, for example, 2:1. By means of this measure, the molar colour-forming capacity of the couplers is increased and a greater colour density is achieved, so that the amount of coupler employed can be reduced and, as a result, at the same time the amount of ballast groups and, thus, their possible adverse influence on the photographic material can be reduced. Colour couplers of this type are known, for example, from U.S. Pat. No. 3,077,403 and German Offenlegungsschrift No. 2,408,168. However, the characteristics of these couplers in use are still not entirely satisfactory. The object of the present invention is, therefore, to provide novel materials for colour photography which have improved characteristics and in which compounds which contain, per molecule, two chromogenic groupings but only one ballast group are employed as the yellow coupler.

The colour couplers employed according to the invention can be either so-called twice 2-equivalent couplers or twice 4-equivalent couplers, i.e. compounds which possess, per molecule, two reactive positions capable of forming a colour with the oxidised developer, 2 or 4 equivalents of silver halide being consumed in each case.

The subject of the present invention is a light-sensitive recording material for colour photography which contains, in at least one silver halide emulsion layer, a yellow coupler of the formula

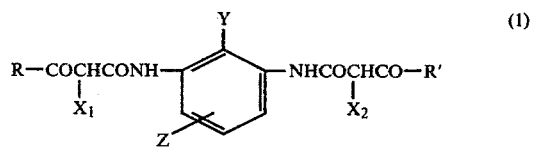

(1)

in which R and R' are alkyl, cycloalkyl or aryl and $X_1$ and $X_2$ are radicals which are detachable during the coupling reaction, Y is halogen, alkyl, alkoxy, alkylmercapto, $-NH_2$, $-NHR_1$, $-NR_1R_2$ $-NHCOR_1$, in which $R_1$ and $R_2$ are alkyl or phenyl, Z is alkyl having 5 to 40 carbon atoms, alkoxy having 5 to 40 carbon atoms, cycloalkoxy having 5 to 12 carbon atoms or aralkyl; alkoxyalkyl, alkoxycycloalkyl, cycloalkoxyalkyl, substituted or unsubstituted phenoxyalkyl, alkylamino- and dialkylamino-alkyl, substituted or unsubstituted arylamino- and diarylamino-alkyl, alkylmercaptoalkyl or substituted or unsubstituted arylmercaptoalkyl, in which radicals the sum of the carbon atoms in each case is 6 to 40; or $-COOR_3$, $-COR_3$, $-NR_3R_4$, $-CONR_3R_4$, $-NR_4COR_3$, $-SO_2R_3$, $-SO_2NR_3R_4$ or $-NR_4SO_2R_3$, $R_3$ is substituted or unsubstituted alkyl having 1 to 40 carbon atoms, substituted or unsubstituted cycloalkyl having 5 to 12 carbon atoms or substituted or unsubstituted phenyl and $R_4$ is hydrogen or alkyl having 1 to 12 carbon atoms.

The invention also relates to a process, for colour photography, for the production of a yellow image by colour development of an exposed recording material which contains a compound of the formula (1) as the yellow coupler, the compounds of the formula (1) and the use of compounds of the formula (1) as yellow couplers in light-sensitive recording materials for colour photography.

Suitable alkyl radicals R and R' in formula (1) can contain 1 to 18 carbon atoms can be straight-chain or branched, for example methyl, ethyl, propyl, i-propyl, butyl, isobutyl, tert.-butyl, amyl, tert.-amyl (1,1-dimethylpropyl), 1,1,3,3-tetramethylbutyl, 1-methyl-1-ethylpentyl, hexyl, 1-methylpentyl, neopentyl, 1-, 2- or 3-methylhexyl, heptyl, n-octyl, tert.-octyl, 2-ethylhexyl, n-nonyl, isononyl, tert.-nonyl, decyl, tert.-decyl and undecyl; and also dodecyl, tetradecyl, hexadecyl and octadecyl as well as the corresponding isomers. Straight-chain or branched alkyl radicals having 3 to 10 carbon atoms are particularly suitable and amongst these tert.-alkyl radicals having 4 to 8 carbon atoms are preferred. tert.-Butyl, 1,1,3,3-tetramethylbutyl, 1-methyl-1-ethylpentyl and 1,1-dimethylpropyl are particularly preferred tertiary alkyl radicals.

Examples of cycloalkyl are those having 3 to 12 ring carbon atoms, for example cyclopropyl, cyclobutyl, cyclopentyl and cyclohexyl, which can be unsubstituted or substituted. Cycloalkyl also includes bicycloalkyl and tricycloalkyl, for example norbornyl and adamantyl. Cyclopentyl, cyclohexyl and adamantyl are preferred.

Aryl radicals are especially phenyl or substituted phenyl, possible substituents being halogen, for example fluorine, chlorine or bromine, and alkyl or alkoxy, preferably each having 1 to 4 carbon atoms, for example methyl, ethyl, propyl, i-propyl, butyl, tert.-butyl, methoxy, ethoxy, propoxy and butoxy, and also amino ($-NH_2$), sulphonyl ($-SO_3H$), alkylsulphonyl and acylamino, the latter two of which can be represented by the formulae $-SO_2R_6$ and $-NHCOR_7$, in which $R_6$ is alkyl having 1 to 5 carbon atoms, for example methyl, ethyl, propyl, i-propyl, butyl or amyl, and $R_7$ is also alkyl having 1 to 5 carbon atoms, particular radicals again being those mentioned for $R_6$.

A preferred aryl radical is phenyl substituted by halogen and alkyl or alkoxy each having 1 to 4 carbon atoms.

Possible radicals $X_1$ and $X_2$, which are detachable during the coupling reaction, are hydrogen (in 4-equivalent couplers), halogen, alkoxy and phenoxy, substituted or unsubstituted, nitrogen-containing 5-membered or 6-membered heterocyclic structures, which are bonded to the coupling point via a nitrogen atom, the radicals $-S-R_8$ and $OPO(OR_9)_2$, in which $R_8$ is alkyl, substituted phenyl or a heterocyclic structure and $R_9$ is alkyl or phenyl, and also a radical of the formula

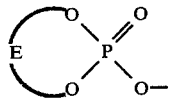

in which E is the complement to a radical containing the ring consisting of the phosphorus atom, the two oxygen atoms and 3 carbon atoms. A suitable detachable halogen is bromine and especially chlorine. The alkoxy radical can contain 1 to 4 carbon atoms and the phenoxy radical can be substituted by nitro, carboxyl or carboxyl-ester, in which the alcohol component of the ester can contain 1 to 4 carbon atoms. Specific examples of carboxyl-ester substituents are methyl, ethyl, propyl and butyl ester groups.

The 5-membered or 6-membered heterocyclic structures which are bonded to the coupling point via a nitrogen atom are, for example, heterocyclic structures which contain one or more nitrogen, sulphur and/or oxygen atoms and, if desired, can be fused to a further ring. Examples which may be mentioned are the radicals of pyrazole, imidazole, triazoles (1,2,3 and 1,2,4), tetrazoles, benztriazole, pyrimidine, pyridazine, thiazole, oxazole and oxazine; and also cyclic imides. The said heterocyclic structures can be in the unsubstituted or substituted form.

Attention is drawn to the following publications with regard to further details relating to leaving groups in two-equivalent yellow couplers:

halogen atoms, such as are described, for example, in German Offenlegungsschrift No. 2,114,577, French Patent Specifications Nos. 991,453 and 869,169 or U.S. Pat. Nos. 2,728,658 and 3,277,155;

the group $-OR$, in which R is alkyl, aryl, a heterocyclic radical or acyl, such as are described, for example, in British Patent Specification No. 1,092,506; French Patent Specifications Nos. 1,411,385 and 1,385,696 or in U.S. Pat. Nos. 3,447,928 and 3,408,194;

the $-SR''$ group which is described in British Patent Specification No. 953,454 or U.S. Pat. No. 3,265,506;

the 1,2,3-benztriazolyl group of the formula

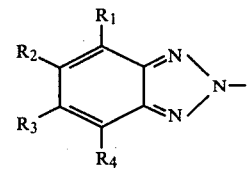

(German Offenlegungsschrift No. 1,800,420)

the radicals $-SO_3H$ and $-SCN$ (British Patent Specification No. 638,039 and U.S. Pat. No 3,253,924)

imide groups of the formulae

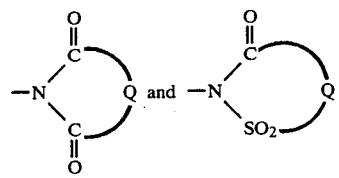

(German Offenlegungsschriften Nos. 2,163,812, 2,213,461 and 2,057,941);

radicals of the formula

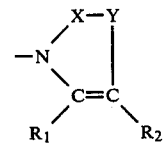

(German Offenlegungsschrift No. 2,329,587)

leaving groups of the formula

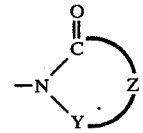

(German Offenlegungsschrift No. 2,433,812)

1,2,4-triazolyl or 1,2,3-benzotriazin-4-(3)-one radicals as leaving groups (German Offenlegungsschrift No. 2,528,638);

1,2,4-triazolyl or tetrazolyl radicals as leaving groups (German Offenlegungsschrift No. 2,442,703), open-chain or cyclic sulphonamidyl radicals as leaving groups (German Offenlegungsschrift No. 2,454,741), leaving groups of the formula

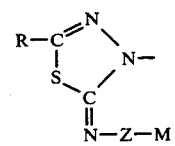

(German Offenlegungsschrift No. 2,716,204) and leaving groups of the formula

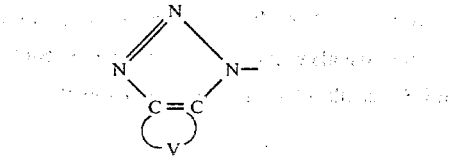

in which V, together with the —C=C— grouping, forms an aromatic ring of the benzene series or a heterocyclic ring containing at least one nitrogen atom (German Offenlegungsschrift No. 2,414,006).

The substituent Y can be halogen, for example fluorine, chlorine or bromine, or alkyl, alkoxy or alkylmercapto, each having, preferably, 1 to 12 carbon atoms, for example methyl, ethyl, propyl, butyl, amyl, hexyl, octyl, nonyl, decyl, undecyl or dodecyl, and the corresponding isomers, and also the analogous alkoxy or alkylmercapto radicals. Further suitable substituents Y are —$NH_2$ and alkyl-, phenyl-, dialkyl- and diphenyl-amino, in which alkyl preferably contains 1 to 5 carbon atoms, or acylamino, in which the acyl radical contains 2 to 13 carbon atoms and as a rule is derived from alkylcarboxylic acids having the corresponding number of carbon atoms or from benzoic acid ($C_6H_5COOH$).

The radical —$NHCOR_{12}$, in which $R_{12}$ is alkyl having 1 to 12 carbon atoms and especially chlorine, are preferred meanings of Y.

The substituent Z, which is in the meta-position, but preferably in the para-position, relative to the substituent Y, can be a straight-chain or branched alkyl radical having 5 to 40 carbon atoms. Possible straight-chain alkyl radicals are thus, for example: pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hentriacontyl, dotriacontyl, tritriacontyl, tetratriacontyl, pentatriacontyl, hexatriacontyl, heptatriacontyl, octatriacontyl, nonatriacontyl and tetracontyl. The corresponding isomers are also suitable.

Z can also be one of the following radicals, in which the sum of the carbon atoms in each case should be in the range of 6 to 40: aralkyl, for example benzyl, alkoxyalkyl, for example $CH_3(CH_2)_4$—$OCH_2$— or $CH_3O(CH_2)_5$— and homologues, alkoxycycloalkyl, for example $CH_3O(cyc)C_5H_8$— and homologues, cycloalkoxyalkyl, for example

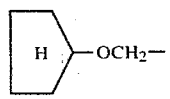

and homologues, phenoxyalkyl, for example

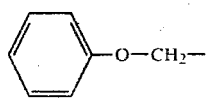

and homologues, which is unsubstituted or substituted by halogen (F, Cl or Br), alkyl or alkoxy ($C_1$–$C_4$); alkyl- and dialkyl-aminoalkyl, for example $CH_3NH(CH_2)_9$—, $C_5H_{11}NHCH_2$—,

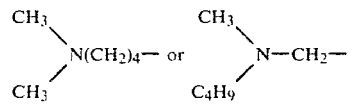

and the corresponding homologues; aryl- and diaryl-aminoalkyl, for example

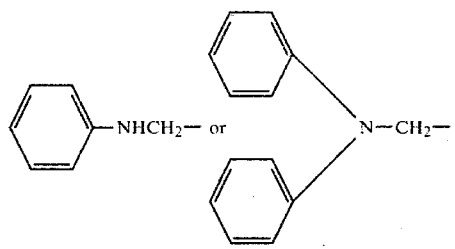

and homologues, which are unsubstituted or substituted in the aryl part by halogen (Cl, Br or I), alkyl or alkoxy ($C_1$–$C_4$), and arylmercaptoalkyl, for example

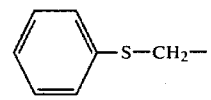

and homologues, which is unsubstituted or substituted as indicated for aryl- and diaryl-aminoalkyl.

Furthermore, Z can be one of the radicals —$COOR_3$, —$COR_3$, —$OR_3$, —$NR_3R_4$, —$CONR_3R_4$, —$NR_4COR_3$, —$SO_2R_3$, —$SO_2NR_3R_4$ or —$NR_4SO_2R_3$, in which $R_3$ is substituted or unsubstituted alkyl having 1 to 40 carbon atoms. Examples of alkyl are methyl, ethyl, propyl and butyl and also the radicals having 5 to 40 carbon atoms mentioned for Z as alkyl. The alkyl groups can also be branched. Possible substituents of the alkyl radicals are phenyl, which is unsubstituted or substituted by alkyl having 1 to 5 carbon atoms, or alkylphenoxy

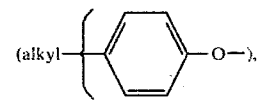

in which the phenyl ring can contain one or more alkyl substituents having, in each case, 1 to 5 carbon atoms. If $R_3$ is cycloalkyl having 5 to 12 carbon atoms, possible radicals are, for example, cyclopentyl, cyclooctyl or cyclododecyl and especially cyclohexyl, which, in turn, can be substituted by alkyl. The alkyl groups can contain 1 to 4 carbon atoms (methyl, ethyl, propyl, isopropyl, butyl, isobutyl or tert.-butyl) and there can be 1 or more, for example 2, of the alkyl substituents on cyclohexyl. Phenyl and phenyl substituted by alkyl are further meanings of $R_3$ and alkyl can contain 1 to 5 carbon atoms (methyl, ethyl, propyl, isopropyl, butyl, isobutyl, tert.-butyl, amyl, isoamyl or tert.-amyl) and one or more alkyl substituents, for example 1 or 2, can be present per phenyl.

$R_4$ is hydrogen or alkyl having 1 to 12 carbon atoms and can be, for example, methyl, ethyl, propyl, butyl, pentyl, hexyl, heptyl, octyl, nonyl, decyl, undecyl or dodecyl or a corresponding isomer (branched alkyl). The radicals —COOR₃, —CONR₃R₄, —NR₄COR₃ and —SO₂NR₃R₄ are preferred.

The substituent Z in compounds of the formula (1) can thus have the following meanings: Z is alkyl having 5 to 40 carbon atoms, alkoxy having 5 to 40 carbon atoms, cycloalkoxy having 5 to 12 carbon atoms or aralkyl; alkoxyalkyl, alkoxycycloalkyl, cycloalkoxyalkyl, substituted or unsubstituted phenoxyalkyl, alkylamino- and dialkylamino-alkyl, substituted or unsubstituted arylamino- and diarylamino-alkyl, alkylmercaptoalkyl or substituted or unsubstituted arylmercaptoalkyl, in which radicals the sum of the carbon atoms in each case is 6 to 40: or —COOR₃, —COR₃, —NR₃R₄, —CONR₃R₄, —NR₄COR₃, —SO₂R₃₃, —SO₂NR₃₃R₄ or NR₄SO₂R₃₃, in which R₃ is substituted or unsubstituted alkyl having 1 to 20 carbon atoms, substituted or unsubstituted cycloalkyl having 5 to 12 carbon atoms or substituted or unsubstituted phenyl, R₃₃ is alkyl having 1 to 20 carbon atoms or substituted or unsubstituted phenyl and R₄ is hydrogen or alkyl having 1 to 12 carbon atoms; or Z is alkyl having 5 to 40 carbon atoms; aralkyl; alkoxyalkyl, alkoxycycloalkyl, cycloalkoxyalkyl, substituted or unsubstituted phenoxyalkyl, alkylamino- and dialkylamino-alkyl, substituted or unsubstituted arylamino- and diarylamino-alkyl, alkylmercaptoalkyl or substituted or unsubstituted arylmercaptoalkyl, in which radical the sum of the carbon atoms in each case is 6 to 40; or —COOR₃, —COR₃, —OR₃, —NR₃R₄, —NR₄COR₃, —SO₂R₃, —SO₂NR₃R₄ or —NR₄SO₂R₃, in which R₃ is straight-chain or branched alkyl having 5 to 40 carbon atoms or cycloalkyl having 5 to 12 carbon atoms and R₄ is hydrogen or straight-chain or branched alkyl having 1 to 12 carbon atoms.

Preferred recording material for colour photography is, now, material of this type which contains, as the yellow coupler, a compound of the formula

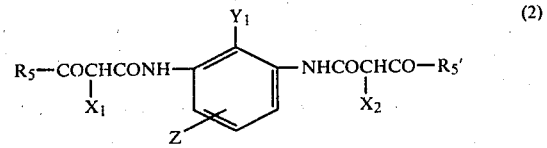

(2)

in which R₅ and R′₅ are straight-chain or branched alkyl having 1 to 18 carbon atoms, cycloalkyl, bicyclo- or tricyclo-alkyl having 3 to 12 ring carbon atoms, phenyl or phenyl substituted by halogen, alkyl or alkoxy each having 1 to 4 carbon atoms, —NH₂, —SO₂R₆ or —NHCOR₇, in which R₆ is alkyl having 1 to 5 carbon atoms and R₇ is alkyl having 1 to 5 carbon atoms, X₁ and X₂ are hydrogen, halogen, substituted or unsubstituted alkoxy and phenoxy, nitrogen-containing 5-membered or 6-membered heterocyclic structures which are bonded to the coupling point via a nitrogen atom, —S—R₈ in which R₈ is alkyl, substituted phenyl or a heterocyclic structure, —OPO(OR₉)₂, in which R₉ is alkyl or phenyl, or a radical of the formula

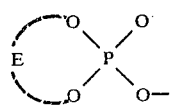

in which E is the complement to a radical containing the six-membered ring consisting of the phosphorus atom, the two oxygen atoms and 3 carbon atoms, Y₁ is fluorine, chlorine, bromine, alkyl, alkoxy and alkylmercapto, each having 1 to 12 carbon atoms, —NH₂, —NHR₁₀, —NR₁₀R₁₁ or —NHCOR₁₂, in which R₁₀ and R₁₁ are alkyl having 1 to 5 carbon atoms or phenyl and R₁₂ is alkyl having 1 to 12 carbon atoms, and Z is as defined.

Particularly suitable recording materials are, furthermore, those which contain the symmetrical couplers of the formula (2), which are of the formula

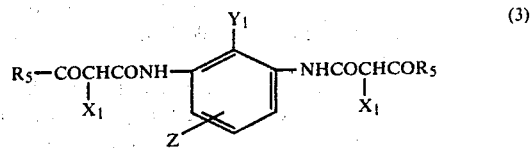

(3)

in which R₅, X₁, Y₁ and Z are as defined.

Further preferred recording materials for colour photography are those which contain, as the yellow coupler, compounds of the formula

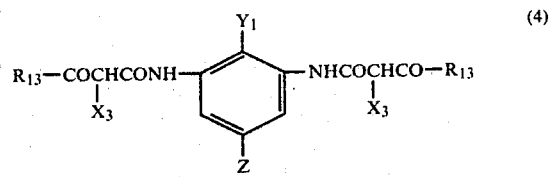

(4)

in which R₁₃ is straight-chain or branched alkyl having 3 to 10 carbon atoms, cyclopentyl, cyclohexyl, adamantyl, phenyl or phenyl substituted by fluorine, chlorine or bromine or alkyl or alkoxy each having 1 to 4 carbon atoms, X₃ is hydrogen, chlorine or a radical of the formulae

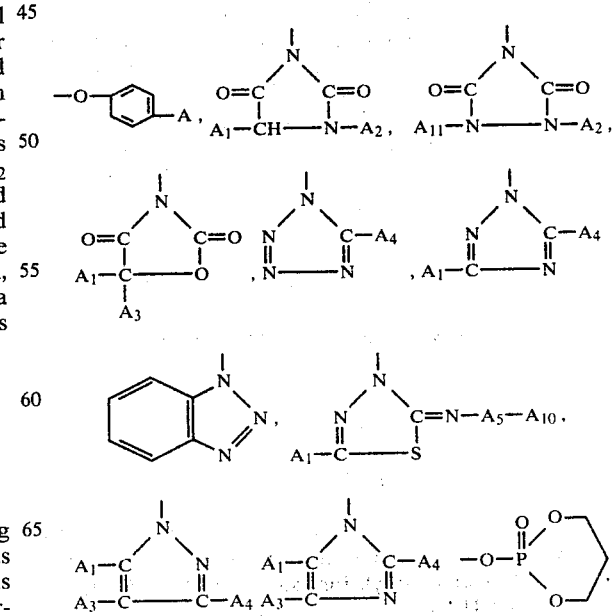

-continued

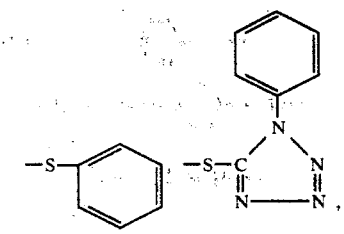

in which A is COOH, NO₂, COOR₁₄, in which R₁₄ is alkyl having 1 to 4 carbon atoms, or the radical of the formula

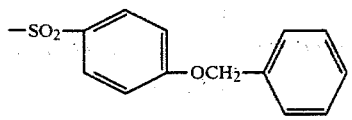

A₁ is hydrogen, alkyl having 1 to 18, and preferably 1 to 4, carbon atoms (methyl, ethyl, propyl, isopropyl, butyl, isobutyl or tert.-butyl), aralkyl, preferably benzyl, aryl, preferably phenyl, cycloalkyl having one to four cycloalkyl rings, alkoxy having 1 to 18 carbon atoms, aryloxy, preferably phenoxy, alkylmercapto having 1 to 18 carbon atoms, arylmercapto, preferably phenylmercapto, halogen, trifluoromethyl, cyano, —NH₂, mono- or di-alkylamino, in which the alkyl radicals each contain 1 to 18 carbon atoms,

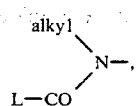

in which alkyl contains 1 to 5 carbon atoms,

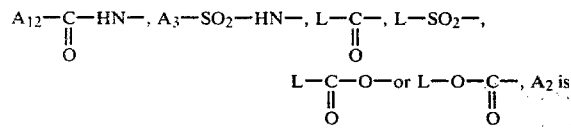

straight-chain or branched alkyl having 1 to 18 carbon atoms, aralkyl, preferably benzyl, or phenyl substituted by alkyl, alkoxy, halogen, —NH₂, alkylamino, dialkylamino, acylamino, —COOH, carbalkoxy, carboxamido, sulphonyl, sulphonamido or alkylmercapto, in which alkyl, alkoxy and acyl preferably each contain 1 to 5 carbon atoms, A₃ is non-branched or branched alkyl having 1 to 18 carbon atoms which is unsubstituted or substituted by halogen, nitro, cyano, alkoxy (C₁-C₄) or primary, secondary or tertiary amino groups, aralkyl, preferably benzyl, or cycloalkyl having one to four cycloalkyl rings; aryl, preferably phenyl, which is unsubstituted or substituted by alkyl or alkoxy each having 1 to 4 carbon atoms, halogen, acylamino (C₁-C₄), —SO₃H, —COOH, sulphonamide or carboxamide, N- or N,N-substituted sulphonamide or carboxamide, preferably alkyl-substituted (C₁-C₄), carboxylic acid ester, hydroxyl, nitro, primary, secondary or tertiary amine, mercapto, alkylmercapto (C₁-C₄), —SO₂—L— or —CO—L; pyridyl, furyl, thienyl, perfluoroalkyl (C₁-C₁₂), acyl, dialkylamino having, in each case, 1 to 5 carbon atoms in the alkyl part, alkoxy having 1 to 18 carbon atoms or phenoxy, A₄ is hydrogen, substituted or unsubstituted alkyl having 1 to 18 carbon atoms, cycloalkyl, preferably cyclohexyl, cycloalkenyl, preferably cyclohexenyl, alkenyl (C₂-C₅), aryl, preferably phenyl, aralkyl, preferably benzyl, a heterocyclic radical, alkoxy (C₁-C₄), aryloxy, preferably phenoxy, alkylmercapto (C₁-C₄), amino which is unsubstituted or substituted by alkyl (C₁-C₄), aryl, preferably phenyl, or acyl, alkylsulphonyl (C₁-C₄), arylsulphonyl, acyloxy, aminosulphonyl, carboxamide, sulphonamide, alkyl carboxylate (C₁-C₄ in the alkyl radical), nitro, cyano, halogen, substituted or unsubstituted ureido or substituted or unsubstituted aminosulphonylamino, A₅ is —CO— or —SO₂— and A₁₀ is hydrogen, if A₅ is —CO—, and has the meaning defined for A₃, A₁₁ is alkyl having 1 to 18 carbon atoms which is unsubstituted or substituted by halogen, amino, cyano or alkoxy (C₁-C₄), and also cycloalkyl, especially cyclohexyl, aryl, especially phenyl, or aralkyl, especially benzyl, A₁₂ is hydrogen and has the meaning defined for A₃ and L is alkyl having 1 to 18 carbon atoms, which is unsubstituted or substituted by halogen, amino, cyano or alkoxy (C₁-C₄), cycloalkyl, preferably cyclohexyl, aryl, preferably phenyl, pyridyl, pyrimidyl, furyl or thienyl and Y₁ and Z are as defined.

Finally, particularly preferred materials for colour photography are those which contain the yellow couplers of the formula

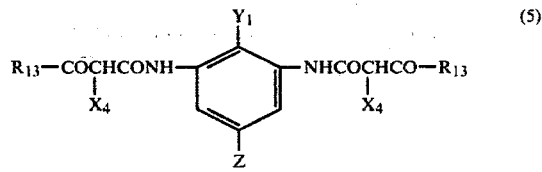

(5)

in which X₄ is hydrogen, chlorine or a radical of the formulae

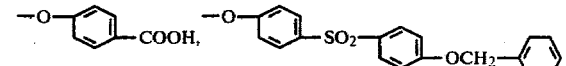

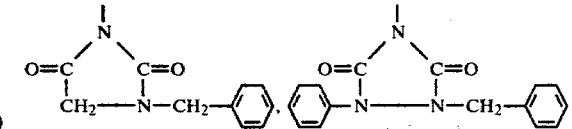

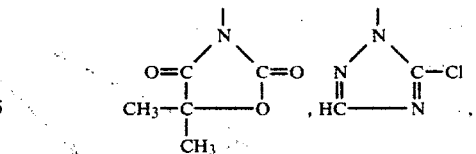

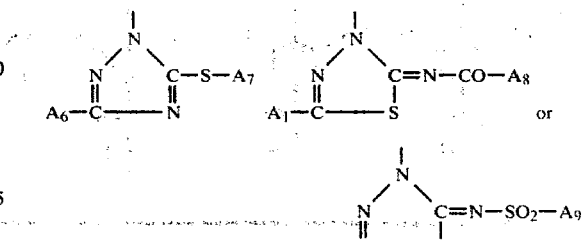

or

in which $A_6$ is hydrogen or alkyl having 1 to 4 carbon atoms, $A_7$ is alkyl having 1 to 12, and preferably 1 to 9, carbon atoms, $A_8$ is straight-chain or branched alkyl having 1 to 18, and preferably 1 to 4, carbon atoms, $-CH_2Cl$, $-CCl_3$, $-CH_2-O-\phi$, $-CH_2-O-\phi-t.C_5H_{11}$, $-CH_2-O-\phi(t.C_5H_{11})(t.C_5H_{11})$, $-CH(C_{12}H_{25})-O-\phi-t.C_5H_{11}$, $-CH(C_{12}H_{25})-O-\phi-t.C_5H_{11}$, $-CH_2-O-C_nH_{2n+1}$, aralkyl, cycloalkyl, phenyl or phenyl substituted by $-C_nH_{2n+1}$, $-OC_nH_{2n+1}$, $-Cl$, $-Br$, $-NHOCC_nH_{2n+1}$, $-NHOC-\phi$, $-SO_2NH_2$, $-SO_2N(C_nH_{2n+1})(C_nH_{2n+1})$, $-SO_2NH(C_nH_{2n+1})$, $-CONH_2$, $-CON(C_nH_{2n+1})(C_nH_{2n+1})$, $-CONH(C_nH_{2n+1})$, $-SO_2CH_3$, $-SO_2-\phi$, $-SO_2-\phi-CH_3$, $-COOH$, $-COOC_nH_{2n+1}$, $-COO-\phi$, $-COO-C_nH_{2n+1}$, $-COO-CH_2-\phi$, $-OH$, $-NH_2$, $-NH(C_nH_{2n+1})$, $-N(C_nH_{2n+1})(C_nH_{2n+1})$, $-SC_nH_{2n+1}$, $-SO_3H$, $COC_nH_{2n+1}$ or $-CO-\phi$;

pyridyl, furyl, thienyl, $-C_nF_{2n+1}$, $-COC_nH_{2n+1}$, $-CO-\phi$, cyclohexyl, norbornyl, adamantyl, $-N(C_nH_{2n+1})(C_nH_{2n+1})$, $-O-C_nH_{2m+1}$ or $-O-\phi$ and n is a number from 1 to 5, $A_9$ is $-CH_3$, $-\phi$, $-\phi-CH_3$ or $-\phi-NHCOCH_3$ and $R_{13}$, $Y_1$, Z and $A_1$ are as defined.

The compounds of the formulae (1) to (5) are also a subject of the present invention.

The preparation of the compounds of the formulae (1) to (5) can be carried out in accordance with the following reaction scheme.

Reaction scheme for the preparation of the couplers

-continued

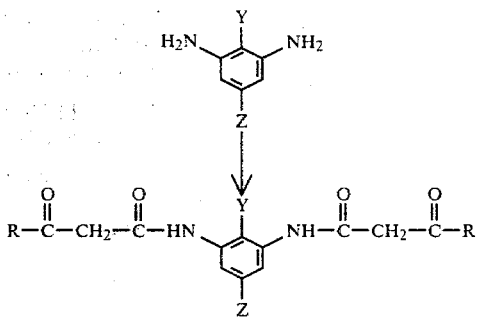

The dinitrobenzoic acids, dinitrosulphonic acids, dinitroamines or dinitrophenols of the formulae

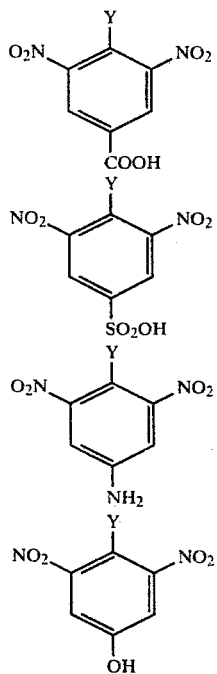

which are required as starting materials are known from the literature. They can be prepared by various methods, such as those described, for example, in Org. Synth. Coll. Vol. 4 364; Ann. 366, 95; Ann. 274, 349; J. Am. Chem. Soc. 49, 497, (1927); Ber. 42, 1729; Ber. 10, 1696 and Ber. 59, 1221.

The dinitrobenzoic acids and dinitrosulphonic acids can be converted via the corresponding acid chlorides, in accordance with the reaction scheme, into the corresponding esters, amides or amines, sulphonates or sulphonamides of the formula

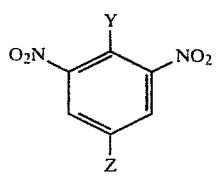

These, in turn, can be reduced by known methods to the corresponding diamines.

Diamines of the formula

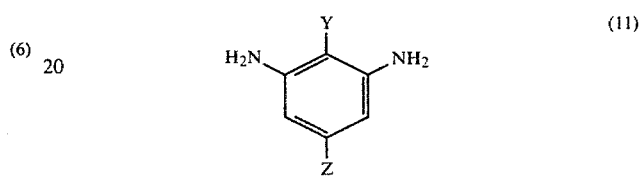

are reacted with at least two mol equivalents of an ester of the formula

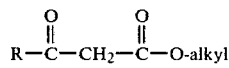

R, Y, and Z are as defined. Esters of the formula (12) are known from the literature (for example U.S. Pat. Nos. 3,245,506 and 27,848, Org. Reactions, 1, 266 et seq.—Wiley New York—and J.A.C.S. 70, 497 (1948)).

They are obtained, for example, by a condensation reaction of an acid chloride of the formula

with the sodium compound of an alkyl acetoacetate and subsequent scission of the reaction product with a base (c.f., for example, German Offenlegungsschriften No. 2,503,099 and 2,114,577, Org. Synth. Coll. Vol. II, 266 and J. Am. Chem. Soc. 67, 2197 (1945)).

The bis-couplers of the formula

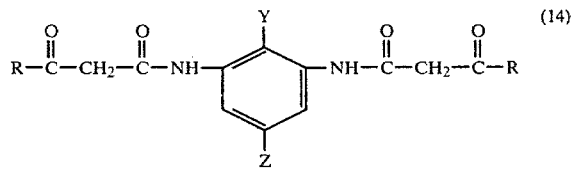

are obtained from the reaction of the keto-esters of the formula (12) with diamines of the type indicated as examples in Table I.

The four-equivalent couplers of the formula (14) obtained by the preparation process described can be modified by replacing one hydrogen of the —CH$_2$— group by a halogen atom in a manner which is known per se. (c.f. German Offenlegungsschriften Nos. 2,263,875, 2,402,220 and 2,329,587 and U.S. Pat. No. 3,265,506).

These two-equivalent couplers are of the formula

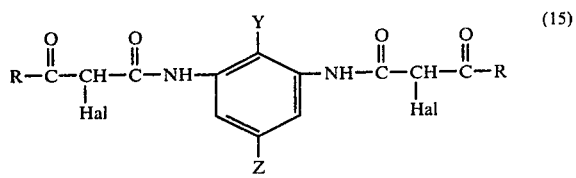

(15)

in which Hal is Cl or Br and R, Y and Z are as defined.

The two-equivalent couplers of the formula (15) can preferably be further reacted with salts of the formula $X^{\ominus} M^{\oplus}$ X is a radical which is detachable during the coupling reaction and M is, for example, Na, K or Ag.

The yellow couplers of the formulae (1) to (5) can be incorporated, in a known manner, in a silver halide emulsion containing gelatine or another binder. Corresponding application possibilities are described, for example, in U.S. Pat. Nos. 2,304,939, 2,304,940, 2,322,027, 2,284,879, 2,801,170, 2,801,171, 2,749,360 and 2,825,382.

If desired, they can also be employed in the developing bath.

The yellow couplers of the formulae (1) to (5) can be used on their own or as a mixture and in some cases even as a mixture with other couplers.

Carrier materials for the light-sensitive recording material, for colour photography, according to the invention having at least one silver halide emulsion layer can be the conventional carriers suitable for this purpose, for example cellulose acetate, polystyrene, polyester (polyethylene terephthalate) or polycarbonate films and also papers, which can be coated, and glass.

The couplers used according to the invention have a high coupling reactivity towards the oxidation product of the aromatic primary amine (developer), so that the developing of the silver halide emulsion proceeds rapidly.

Furthermore, an adequate colour density is achieved, although the molar amount of coupler employed can be markedly reduced compared with that of known couplers. Since, at the same time, the amount of solvent for the coupler can be reduced, it is possible to reduce the total layer thickness of the emulsion layer.

If two-equivalent couplers are used, it is also possible to reduce the amount of silver halide. All of the measures lower the production costs for the photographic material.

The layer sensitive to blue light can be kept thinner and by this means the sharpness and the resolution of the resulting colour image are improved.

The coloured photographic image obtained with the yellow couplers employed according to the invention displays a good resistance to light and moisture and a stability sufficiently great to enable it to be stored for a prolonged period without any impairment.

PREPARATION INSTRUCTIONS FOR THE PREPARATION OF THE DIAMINES

Preparation Instructions 1

Stage 1

13.25 g of 4-chloro-3,5-dinitro-benzoyl chloride and 10.25 g of dodecan-1-ol are dissolved in 150 ml of benzene and the solution is stirred in the presence of 4.5 g of pyridine for one hour at 20° C. The mixture is then washed with water and subsequently dried. After evaporating off the benzene, the resulting crude product is recrystallised from methanol. This gives 18.5 g of a white product. Melting point 49° to 52° C.

Stage 2

20 g of iron powder, 25 ml of water and 5 ml of hydrochloric acid are refluxed for 90 minutes. The mixture is cooled to about 40° C. A solution of 10 g of dodecyl 4-chloro-3,5-dinitro-benzoate in methanol is then added. The mixture is refluxed for 4 hours and then filtered hot. Water is added to the filtrate until it becomes turbid; the mixture is then cooled with ice and filtered. This gives 7.5 g of a light brown powder.

Melting point: 70° to 73° C. (diamine 101 in Table I)

Preparation Instructions 2

Stage 1

14.5 g of 4-chloro-3,5-dinitro-benzoyl chloride are dissolved in 200 ml of diethyl ether and the solution is cooled to −10° C. A solution of 10 g of dodecylamine and 5.5 g of triethylamine, dissolved in 200 ml of ether, is added dropwise to this solution in the course of 3 hours. The mixture is stirred for a further one hour, during which time the temperature rises to about 20° C. The mixture is washed with water and then dried and the solvent is then removed. The product is recrystallised from ethyl acetate/hexane. This gives 18 g of a light yellow product.

Melting point: 87° to 90° C.

Stage 2

The product obtained from Stage 1 is reduced analogously to Stage 2 in Preparation Instructions 1. This gives 4-chloro-3,5-diamino-benzoic acid dodecylamide.

Melting point: 102° to 105° C. (Diamine 108 in Table I).

The other diamines listed in Table I are prepared analogously from the corresponding starting materials.

TABLE I

Diamines of the formula

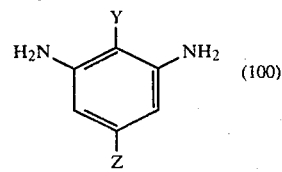

| No. | Y | Z | Melting point °C. |
|---|---|---|---|
| 101 | Cl | —COO(CH₂)₁₁CH₃ | 70–73 |
| 102 | Cl | —COOCH₂C(CH₃)₃ | 108–110 |

TABLE I-continued

Diamines of the formula $$H_2N-C_6H_2(Y)(NH_2)-Z \quad (100)$$

(2,6-diamino substituted benzene with Y at position and Z at position)

| No. | Y | Z | Melting point °C |
|---|---|---|---|
| 103 | $CH_3$— | —$COO(CH_2)_{11}CH_3$ | 67–70 |
| 104 | $CH_3O$— | —$COO(CH_2)_{11}CH_3$ | 55–57 |
| 105 | Cl | —COO—$C_6H_4$—$C(CH_3)_2CH_2CH_3$ | 81–84 |
| 106 | Cl | —COO—$(CH_2)_4$—O—$C_6H_3$[$C(CH_3)_2CH_2CH_3$]$_2$ | 117–118 |
| 107 | Cl | —COO—(cyclohexyl-H)($CH_3$)($C(CH_3)_3$) | 118–122 |
| 108 | Cl | —$CONH(CH_2)_{11}CH_3$ | 102–105 |
| 109 | Cl | —CONH—$(CH_2)_4$—O—$C_6H_3$[$C(CH_3)_2CH_2CH_3$]$_2$ | 120–122 |
| 110 | H | —CONH—$(CH_2)_4$—O—$C_6H_3$[$C(CH_3)_2CH_2CH_3$]$_2$ | 105–106 |
| 111 | Cl | —$CON[(CH_2)_5CH_3]_2$ | 67–68 |
| 112 | Cl | —$CON[(CH_2)_7CH_3]_2$ | 32–33 |
| 113 | Cl | —CON($CH_3$)—$(CH_2)_{11}CH_3$ | 41–42 |
| 114 | Cl | —CON[$C(CH_3)_3$]—$(CH_2)_7CH_3$ | Oel |
| 115 | Cl | —NH—CO—$(CH_2)_{10}CH_3$ | 110–112 |
| 116 | Cl | —NH—CO—CH($C_{12}H_{25}$)—O—$C_6H_4$—$C(CH_3)_2CH_2CH_3$ | 42–43 |
| 117 | $CH_3$ | —$SO_2NH$—$(CH_2)_{11}CH_3$ | 61–64 |
| 118 | Cl | —CON$\pm$($CH_2$—$CH_2$—$CH_2$—$CH_3$)$_2$ | 128–130 |
| 119 | Cl | —CON$\pm$[$CH_2$—CH($CH_3$)$_2$]$_2$ | 119–122 |
| 120 | Cl | —CON$\pm$[$CH_2$—CH($C_2H_5$)—$(CH_2)_3$—$CH_3$]$_2$ | 67–71 |
| 121 | Cl | —CON$\pm$[CH($CH_3$)—$CH_2$—$CH_3$]$_2$ | 137–139 |
| 122 | Cl | —CON$\pm$($CH_2$—$CH_3$)$_2$ | 111–112 |
| 123 | Cl | —CON$\pm$[CH($CH_3$)$_2$]$_2$ | 129–131 |
| 124 | Cl | —COO—$C_6H_5$ | 140–142 |

Preparation of the yellow couplers

EXAMPLE 1

A solution of 10 g of dodecyl 4-chloro-3,5-diaminobenzoate (Diamine No. 101) and 10 g of methyl pivaloylacetate are heated in 150 ml of xylene to 140° C. for 5 hours. During this period, the alcohol formed is continuously removed by distillation. After the reaction has ended, the xylene is evaporated; the residue is recrystallised from methanol.

A product which melts at 64° to 65° C. is obtained. (Coupler No. 201 in Table II).

The $D_{max}$ values for the dyes obtained from the couplers (c.f. Example 10) are also given in the tables which follow.

EXAMPLE 2

A solution of 8 g of isobutyl 4-chloro-3,5-diaminobenzoate (Diamine No. 102) and 28 g of ethyl o-ethoxybenzoylacetate in 300 ml of xylene are heated to 140° C. for 3 hours, the ethanol formed being distilled off. After the reaction has ended, the xylene is evaporated and the residue is treated in methanol with active charcoal and the mixture is then filtered. After crystallisation from methanol/chloroform, 13.5 g of a product which melts at 142° to 145° C. are obtained. (Coupler No. 208 in Table II).

EXAMPLE 3

A solution of 67 g of 4-chloro-3,5-diamino-N,N-di(2-ethylhexylamine)-benzoic acid amide (Diamine No. 120) and 77 g of methyl pivaloylacetate are refluxed in 1,000 ml of xylene for 5 hours. During this period the alcohol is removed continuously by distillation. The xylene is evaporated. The crude product is recrystallised from methanol. This gives a product which melts at 40° to 45° C. (Coupler No. 221 in Table II).

A further product which has a melting point of 84° to 87° C. and is of the formula

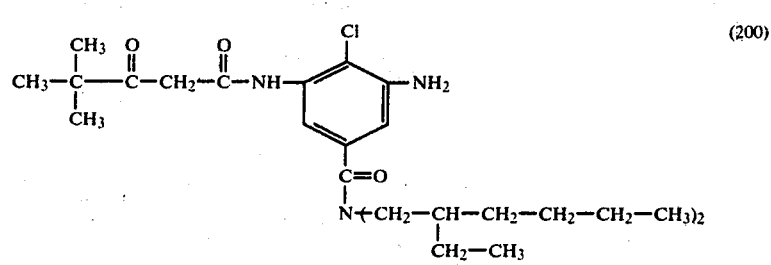

(200)

was obtained from the mother liquor.

The other couplers listed in Table II can also be prepared in an analogous manner.

TABLE II

Yellow couplers of the formula

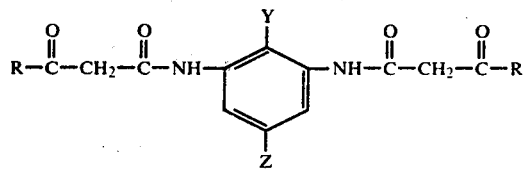

| No. | R | Z | Y | Melting point °/146-$D_{max}$ | |
|---|---|---|---|---|---|
| 201 | t-Butyl | —COO—(CH$_2$)$_{11}$—CH$_3$ | Cl | 64–65 | 1.33 |
| 202 | t-Butyl | —COO—(CH$_2$)$_{11}$—CH$_3$ | CH$_3$— | 82–85 | 0.88 |
| 203 | t-Butyl | —COO—(CH$_2$)$_{11}$—CH$_3$ | CH$_3$O— | 54–56 | 0.74 |
| 204 | t-Butyl | —COO—CH$_2$—C(CH$_3$)$_3$ | Cl | 139–141 | 1.17 |
| 205 | t-Butyl | —COO—⟨H⟩—CH$_3$ , C(CH$_3$)$_3$ | Cl | 94–96 | 0.99 |
| 206 | t-Butyl | —COO—(CH$_2$)$_4$—O—⟨t-C$_5$H$_{11}$, t-C$_5$H$_{11}$⟩ | Cl | 51–53 | 1.26 |
| 207 | CH$_3$(CH$_2$)$_3$—C(CH$_3$)(CH$_2$CH$_3$)— | —COO—CH$_2$—C(CH$_3$)$_3$ | Cl | 72–74 | 0.91 |
| 208 | ⟨OCH$_2$CH$_3$-phenyl⟩ | —COO—CH$_2$—C(CH$_3$)$_3$ | Cl | 142–145 | 0.99 |
| 209 | t-Butyl | —CONH—(CH$_2$)$_{11}$CH$_3$ | Cl | 140–143 | 1.32 |
| 210 | t-Butyl | —CONH—(CH$_2$)$_4$—O—⟨t-C$_5$H$_{11}$, t-C$_5$H$_{11}$⟩ | H | 100–103 | 0.97 |
| 211 | t-Butyl | —CONH—(CH$_2$)$_4$—O—⟨t-C$_5$H$_{11}$, t-C$_5$H$_{11}$⟩ | Cl | 173–175 | 1.17 |

TABLE II-continued

Yellow couplers of the formula $$R-\underset{\underset{O}{\|}}{C}-CH_2-\underset{\underset{O}{\|}}{C}-NH-\text{[benzene with Y, Z]}-NH-\underset{\underset{O}{\|}}{C}-CH_2-\underset{\underset{O}{\|}}{C}-R$$

| No. | R | Z | Y | Melting point °146-D$_{max}$ | |
|---|---|---|---|---|---|
| 212 | t-Butyl | —CON$\big<$(CH$_2$)$_5$CH$_3$ / (CH$_2$)$_5$CH$_3$ | Cl | 124–126 | 1.54 |
| 213 | t-Butyl | —NH—CO—CH(—(CH$_2$)$_{11}$CH$_3$)—O—C$_6$H$_4$—t-C$_5$H$_{11}$ | Cl | 75–77 | 1.27 |
| 214 | t-Butyl | —SO$_2$—NH—(CH$_2$)$_{11}$CH$_3$ | CH$_3$— | 101–103 | 1.15 |
| 215 | t-Butyl | —CON—(CH$_2$)$_7$CH$_3$, CH$_3$—C(CH$_3$)—CH$_3$ | Cl | 140–142 | 1.31 |
| 216 | Adamantyl | C(CH$_3$)$_2$CH$_2$CH$_3$; —CONH—(CH$_2$)$_4$—O—C$_6$H$_4$—C(CH$_3$)$_2$CH$_2$CH$_3$ | Cl | 175–178 | 0.61 |
| 217 | t-Butyl | —CON(—CH$_3$)—(CH$_2$)$_{17}$—CH$_3$ | Cl | Oil | 1.12 |
| 218 | t-Butyl | —COO—C$_6$H$_5$ | Cl | 214–216 | 0.70 |
| 219 | t-Butyl | —CON$\big[$—CH(CH$_3$)$_2\big]_2$ | Cl | 204–206 | 1.27 |
| 220 | t-Butyl | —CON(—CH$_2$—CH$_3$)$_2$ | Cl | 175–176 | 0.98 |
| 221 | t-Butyl | —CON$\big[$—CH$_2$—CH(C$_2$H$_5$)—(CH$_2$)$_3$—CH$_3\big]_2$ | Cl | 40–45 | 1.20 |
| 222 | t-Butyl | —CON$\big[$—C(CH$_3$)—CH$_2$—CH$_3\big]_2$ | Cl | 69–71 | 1.09 |
| 223 | t-Butyl | —CON(—CH$_2$—CH$_2$—CH$_2$—CH$_3$)$_2$ | Cl | amorphous | 1.11 |
| 224 | t-Butyl | —CON$\big[$—CH$_2$—CH(CH$_3$)$_2\big]_2$ | Cl | 110–113 | 1.08 |

EXAMPLE 4

Dodecyl 3,5-bis-[α-chloro-α-pivaloyl-acetamido]-4-chloro-1-benzoate 0.38 g of sulphuryl chloride was added dropwise at −10° C. to a solution of 0.85 g of dodecyl 3,5-bis-[α-pivaloylacetamido]-4-chloro-1-benzoate (Coupler No. 201) in 30 ml of benzene/hexane. The mixture is stirred for a further half hour at −10° C. The reaction mixture is then warmed to room temperature and stirred for a further one hour. The solvent is distilled off and the residue is recrystallised from methanol. 820 mg of Coupler No. 301 are obtained.

Melting point: 110° to 115° C.

EXAMPLE 5

Dodecyl 3,5-bis-[α-bromo-α-pivaloyl-acetamido]-4-chloro-1-benzoate 118 g of bromine were added slowly dropwise at −5° C. to a solution of 225 g of Coupler No. 201 in 600 ml of carbon tetrachloride. The icebath is then removed and, after warming to room temperature, the reaction mixture is stirred for a further one hour. The solution is washed, first with dilute sodium hydroxide solution and then with water, and dried. After removing the solvent, Coupler No. 302 is obtained in the form of a yellowish powder having a melting point of 102° to 107° C.

The other yellow couplers in Table III can be prepared in the same way.

TABLE III

Yellow couplers of the formula

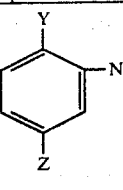

| No. | R | Z | Y | X | Melting point °C. | $D_{max}$ |
|---|---|---|---|---|---|---|
| 301 | t-Butyl | —COO—(CH$_2$)$_{11}$CH$_3$ | Cl | Cl | 110–115 | 1.08 |
| 302 | t-Butyl | —COO—(CH$_2$)$_{11}$CH$_3$ | Cl | Br | 100–102 | 1.05 |
| 303 | t-Butyl | —COO—(CH$_2$)$_{11}$CH$_3$ | CH$_3$O— | Cl | 101–102 | 0.86 |
| 304 | t-Butyl | —COO—(CH$_2$)$_{11}$CH$_3$ | CH$_3$— | Cl | 143–145 | 0.53 |
| 305 | t-Butyl | —COO—(CH$_2$)$_{11}$CH$_3$ | CH$_3$— | Br | 124–126 | 0.75 |
| 306 | t-Butyl | 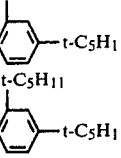 | Cl | Cl | 44–45 | 1.11 |
| 307 | t-Butyl |  | Cl | Br | 51–53 | 0.91 |
| 308 | t-Butyl | —COO—CH$_2$—C(CH$_3$)$_3$ | Cl | Cl | 53–54 | 0.95 |
| 309 | t-Butyl | —COO—CH$_2$—C(CH$_3$)$_3$ | Cl | Br | 55–59 | 0.96 |
| 310 | 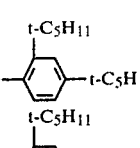 | —COO—CH$_2$—C(CH$_3$)$_3$ | Cl | Cl | 30–32 | 0.85 |
| 311 | 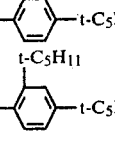 | —COO—CH$_2$—C(CH$_3$)$_3$ | Cl | Cl | 42–45 | 1.21 |
| 312 | t-Butyl | —CONH(CH$_2$)$_{11}$CH$_3$ | Cl | Cl | 112–113 | 1.04 |
| 313 | t-Butyl | 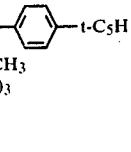 | Cl | Cl | 136–138 | 1.37 |
| 314 | t-Butyl |  | Cl | Br | 138–140 | 1.21 |
| 315 | t-Butyl |  | H | Cl | 81–82 | 0.21 |
| 316 | t-Butyl | —NH—CO—CH$_2$—O—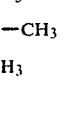—t-C$_5$H$_{11}$ | Cl | Cl | 103–104 | 1.12 |
| 317 | t-Butyl | —SO$_2$—NH—(CH$_2$)$_{11}$CH$_3$ | CH$_3$— | Cl | 77–80 | 0.89 |
| 318 | 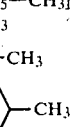 | —COO—CH$_2$—C(CH$_3$)$_3$ | Cl | Br | 55–58 | 0.93 |
| 319 | t-Butyl | 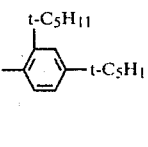 | Cl | Cl | 50–52 | 1.01 |
| 320 | t-Butyl | " | Cl | Br | 193–195 | 0.98 |
| 321 | t-Butyl | —CON[(CH$_2$)$_5$—CH$_3$]$_2$ | Cl | Cl | Oil | 1.15 |
| 322 | t-Butyl |  | Cl | Cl | 68–70 | 0.92 |
| 323 | CH$_3$—(CH$_2$)$_3$—C(CH$_3$)(CH$_2$CH$_3$)— | —COO—(CH$_2$)$_4$—O—⟨⟩—t-C$_5$H$_{11}$ (with t-C$_5$H$_{11}$) | Cl | Cl | Oil | 0.50 |

TABLE III-continued

Yellow couplers of the formula $$R-\underset{\underset{X}{|}}{\overset{O}{\overset{\|}{C}}}-CH-\overset{O}{\overset{\|}{C}}-NH-\underset{\underset{Z}{}}{\overset{Y}{\bigcirc}}-NH-\overset{O}{\overset{\|}{C}}-\underset{\underset{X}{|}}{CH}-\overset{O}{\overset{\|}{C}}-R'$$

| No. | R | Z | Y | X | Melting point °C. | $D_{max}$ |
|---|---|---|---|---|---|---|
| 324 | " | " | Cl | Br | 48–50 | 0.42 |
| 325 | Adamantyl | —CONH—(CH$_2$)$_4$—O—⟨C$_6$H$_3$⟩(C(CH$_3$)$_2$CH$_2$CH$_3$)$_2$ | Cl | Cl | 122–125 | 0.73 |
| 326 | Adamantyl | —CONH—(CH$_2$)$_4$—O—⟨C$_6$H$_3$⟩(C(CH$_3$)$_2$CH$_2$CH$_3$)$_2$ | Cl | Br | 136–138 | 0.81 |
| 327 | t-Butyl | —CON(CH(CH$_2$CH$_3$)$_2$)$_2$ | Cl | Cl | 240–242 | 1.09 |
| 328 | t-Butyl | —CON(CH(CH$_3$)—CH$_2$—CH$_3$)$_2$ | Cl | Cl | 52–55 | 0.68 |
| 329 | t-Butyl | —CON(CH$_2$—CH$_2$—CH$_2$—CH$_3$)$_2$ | Cl | Br | 50–55 | 1.15 |
| 330 | t-Butyl | —CON(CH$_2$—CH(CH$_3$)$_2$)$_2$ | Cl | Br | 50–52 | 1.02 |
| 331 | t-Butyl | —CON(CH(CH$_3$)$_2$)$_2$ | Cl | Br | 224–228 | 1.04 |
| 332 | t-Butyl | —COO—⟨C$_6$H$_5$⟩ | Cl | Br | 52–55 | 0.71 |
| 333 | t-Butyl | —CON(CH(CH$_3$)—CH$_2$—CH$_3$)$_2$ | Cl | Br | 188–190 | 1.05 |
| 334 | t-Butyl | —CONH(CH$_2$)$_{11}$—CH$_3$ | Cl | Br | 160–163 | 101 |

EXAMPLE 6

Dodecyl 3,5-bis-[α-(5-chloro-1,2,4-triazolyl)-α-pivaloylacetamido]-4-chloro-1-benzoate A mixture of 0.780 mg of the potassium salt of 5-chloro-1,2,4-triazole and 1.4 g of dodecyl 3,5-bis-(α-bromo-α-pivaloyl-acetamido)-4-chloro-1-benzoate is stirred in 50 ml of absolute acetonitrile for 6 hours at room temperature. The yellow suspension is poured into 500 ml of acidified water (pH value: 2.5); the resulting white precipitate is then filtered off. After recrystallisation from ethyl acetate/hexane, 1.1 g of the compound of the formula

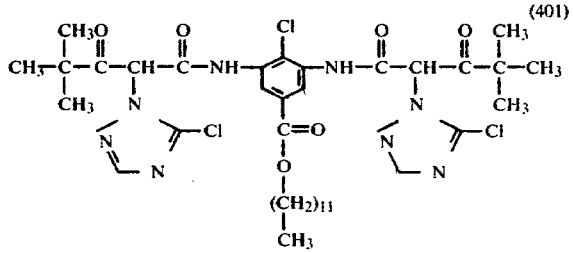

(401)

are obtained.

Melting point: 148° to 150° C.

EXAMPLE 7

The potassium salt of 2-p-toluenesulphonylamino-5-isopropyl-1,3,4-thiadiazole is reacted, in accordance with Example 5, with the benzoate mentioned in Example 6. This gives the coupler of the formula

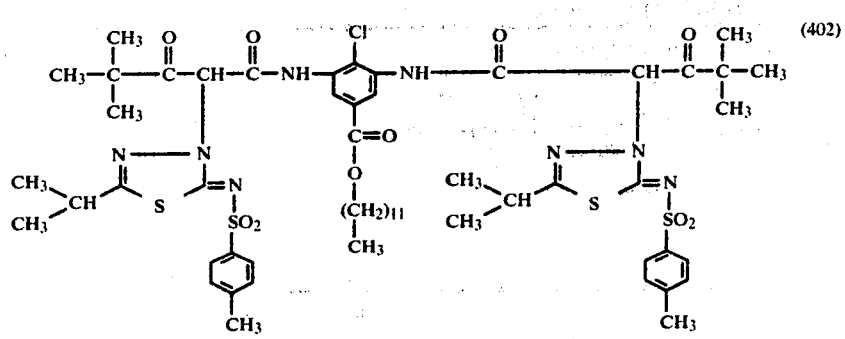
Melting point: 146° to 148° C.
The other compounds mentioned in Table IV can also be prepared in an analogous manner.
(Reaction of halogen-substituted couplers of the formula
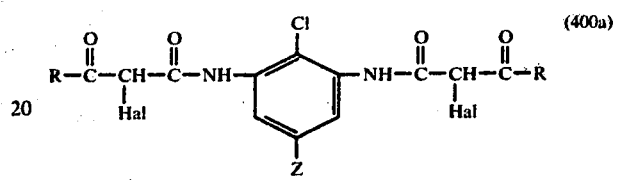
in corresponding solvents with salts of the formula (400b) (X⊖ M⊕).

TABLE IV

Yellow couplers of the formula

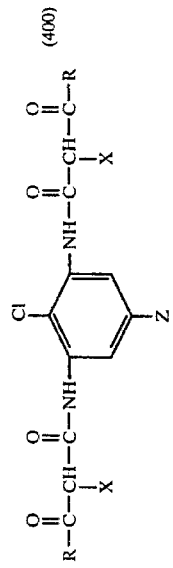

| No. | R | Z | X | Melting point °C. | $D_{max}$ |
|---|---|---|---|---|---|
| 403 | t-Butyl | —COO—(CH$_2$)$_{11}$CH$_3$ | (structure with N=N, CH(CH$_3$)$_2$, S, N=SO$_2$–C$_6$H$_4$–CH$_3$) | 146–148 | 1.46 |
| 404 | t-Butyl | —COO—(CH$_2$)$_{11}$CH$_3$ | (structure with triazole, Cl) | 148–150 | 1.35 |
| 405 | t-Butyl | —COO—(CH$_2$)$_{11}$CH$_3$ | (structure with N, S, phenyl, N=C(O)C(CH$_3$)$_3$) | 113–115 | 1.43 |
| 406 | t-Butyl | —COO(CH$_2$)$_4$–O–C$_6$H$_3$(t-C$_5$H$_{11}$)$_2$ | (structure with (CH$_3$)$_3$C, S, N=C(O)C(CH$_3$)$_3$) | 163–164 | 1.45 |
| 407 | t-Butyl | —COO(CH$_2$)$_4$–O–C$_6$H$_3$(t-C$_5$H$_{11}$)$_2$ | (structure with CH(CH$_3$)$_2$, S, N=SO$_2$–C$_6$H$_4$–CH$_3$) | 173–176 | 1.42 |

TABLE IV-continued

Yellow couplers of the formula $$\begin{array}{c}\text{R—C—CH—C—NH} \\ \| \quad | \quad \| \\ \text{O} \quad \text{X} \quad \text{O}\end{array} \begin{array}{c}\text{Cl} \\ \diagup\!\!\!\diagdown \\ \diagdown\!\!\!\diagup \\ \text{NH—C—CH—C—R} \\ \| \quad | \quad \| \\ \text{O} \quad \text{X} \quad \text{O}\end{array} \text{Z} \quad (400)$$

| No. | R | Z | X | Melting point °C. | $D_{max}$ |
|---|---|---|---|---|---|
| 408 | t-Butyl | —COO—CH₂—C(CH₃)₃ | (N-benzyl hydantoin) | 193–195 | 0.91 |
| 409 | CH₃(CH₂)₃—C(CH₃)(CH₂CH₃)— | —COO—CH₂—C(CH₃)₃ | (SCH₃ triazole) | 62–65 | 1.18 |
| 410 | t-Butyl | —CONH—(CH₂)₄—O—(2,4-di-t-C₅H₁₁-phenyl) | (N=N, C(CH₃)₂, S, C(O)NHC(CH₃)₃) | 110–112 | 1.42 |
| 411 | t-Butyl | —COO—CH₂—C(CH₃)₃ | (N=N, CH(CH₃)₂, S, C—N—SO₂—C₆H₄—CH₃) | 115–118 | 1.11 |
| 412 | t-Butyl | —COO—(CH₂)₁₁CH₃ | (o-OCH₂CH₃ phenyl, N-benzyl hydantoin) | 141–143 | 1.21 |

TABLE IV-continued
Yellow couplers of the formula
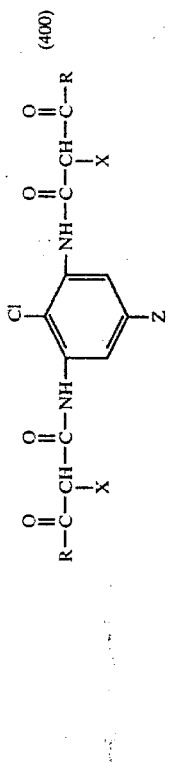
| No. | R | Z | X | Melting point °C. | $D_{max}$ |
|---|---|---|---|---|---|
| 413 | t-Butyl | —CONH—(CH$_2$)$_4$—O—(2-t-C$_5$H$_{11}$, 4-t-C$_5$H$_{11}$-phenyl) | N-phenyl succinimide | 114–115 | 1.26 |
| 414 | Adamantyl | —CONH—(CH$_2$)$_4$—O—(2-t-C$_5$H$_{11}$, 4-t-C$_5$H$_{11}$-phenyl) | (CH$_3$)$_3$C— thiadiazole —N=COC(CH$_3$)$_3$ | 185–188 | 0.96 |
| 415 | CH$_3$(CH$_2$)$_3$—C(CH$_3$)$_2$—CH$_3$ | —CONH—(CH$_2$)$_4$—O—(2-C(CH$_3$)$_2$CH$_2$CH$_3$, 4-C(CH$_3$)$_2$CH$_2$CH$_3$-phenyl) | thiadiazole —N=SO$_2$—C$_6$H$_4$—CH$_3$ | 127–129 | 1.32 |

TABLE IV-continued
Yellow couplers of the formula
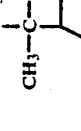
| No. | R | Z | X | Melting point °C. | $D_{max}$ |
|---|---|---|---|---|---|
| 416 | t-Butyl | 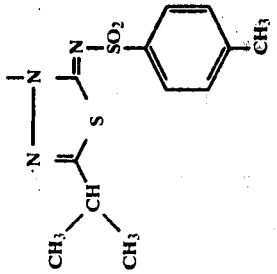 | 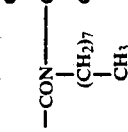 | 122-125 | 1.57 |
| 417 | t-Butyl | 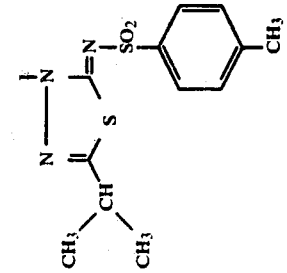 |  | 78-80 | 1.52 |
| 418 | t-Butyl | —CON(CH$_2$—CH$_3$)$_2$ | 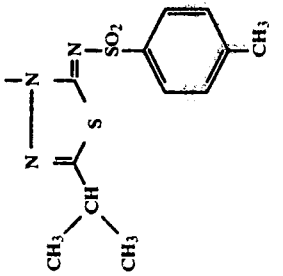 | 157-160 | 1.40 |

TABLE IV-continued

Yellow couplers of the formula $$R-CO-CH(X)-CO-NH-\text{[2-Cl, 5-Z phenyl]}-NH-CO-CH(X)-CO-R \quad (400)$$

| No. | R | Z | X | Melting point °C. | $D_{max}$ |
|---|---|---|---|---|---|
| 419 | t-Butyl | $-CON(CH(CH_3)_2)_2$ | 3-[(4-methylphenyl)sulfonylimino]-5-isopropyl-1,3,4-thiadiazol-2-yl (S-linked) | 148–150 | 1.39 |
| 420 | t-Butyl | $-CON(CH(CH_3)_2)_2$ | 3-(pivaloylimino)-5-t-butyl-1,3,4-thiadiazol-2-yl (S-linked) | 154–157 | 1.25 |
| 421 | t-Butyl | $-CON(CH_2-CH_3)_2$ | 3-(pivaloylimino)-5-t-butyl-1,3,4-thiadiazol-2-yl (S-linked) | 128–131 | 1.11 |

TABLE IV-continued
Yellow couplers of the formula
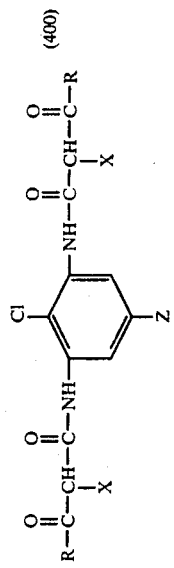
(400)
| No. | R | Z | X | Melting point °C. | $D_{max}$ |
|---|---|---|---|---|---|
| 422 | t-Butyl | —CONH—(CH₂)₄—O—[2-t-C₅H₁₁, 4-t-C₅H₁₁-phenyl] | [4-methoxyphenyl-SO₂-4-phenoxyphenyl] | 114–116 | 1.33 |
| 423 | t-Butyl | —CON(CH(CH₃)CH₂—CH₃)₂ | [thiadiazole with C(CH₃)₃ and C(CH₃)₃ groups, N—CO—C(CH₃)₃] | 175–180 | 1.42 |

TABLE IV-continued

Yellow couplers of the formula $$\underset{R-\underset{X}{\overset{O}{\overset{\|}{C}}}-\overset{}{\overset{}{C}}H-\underset{}{\overset{O}{\overset{\|}{C}}}-NH}{}\underset{}{\overset{Cl}{\underset{Z}{\bigcirc}}}\underset{}{\overset{}{NH-\underset{}{\overset{O}{\overset{\|}{C}}}-\overset{}{\overset{}{C}}H-\underset{X}{\overset{O}{\overset{\|}{C}}}-R}} \quad (400)$$

| No. | R | Z | X | Melting point °C. | $D_{max}$ |
|---|---|---|---|---|---|
| 424 | t-Butyl | —CON(CH—CH$_2$—CH$_3$)$_2$<br>         \|<br>         CH$_3$ | [structure: thiadiazole with SO$_2$-C$_6$H$_4$-CH$_3$ and CH(CH$_3$)$_2$] | 218–221 | 1.46 |
| 425 | t-Butyl | —CON(CH$_2$—CH—(CH$_2$)$_3$—CH$_3$)$_2$<br>           \|<br>           C$_2$H$_5$ | [structure: thiadiazole with SO$_2$-C$_6$H$_4$-CH$_3$ and H] | 108–110 | 1.14 |
| 426 | t-Butyl | —CONH—(CH$_2$)$_{11}$—CH$_3$ | [structure: thiadiazole with C(CH$_3$)$_3$ and C(O)-C(CH$_3$)$_3$] | 93–95 | 1.28 |

TABLE IV-continued

Yellow couplers of the formula $$\underset{R-C-CH-C-NH}{\overset{O\quad O}{\|\quad\|}}\underset{X}{}\overset{Cl}{\underset{Z}{\bigodot}}\underset{NH-C-CH-C-R}{\overset{O\quad O}{\|\quad\|}}\underset{X}{} \quad (400)$$

| No. | R | Z | X | Melting point °C. | $D_{max}$ |
|---|---|---|---|---|---|
| 427 | t-Butyl | −CON(CH₂−CH(CH₃)₂)₂ | [4-methylphenylsulfonyl-iminothiazoline with isopropyl] | 140−142 | 1.35 |
| 428 | t-Butyl | −CON(CH₂−CH₂−CH₂−CH₃)₂ | [4-methylphenylsulfonyl-iminothiazoline with isopropyl] | 193−195 | 1.32 |
| 429 | t-Butyl | $\underset{CH_3}{\overset{O}{\underset{\|}{-C-N(CH-CH_2-CH_3)_2}}}$ | −O−⬡−COOH | 108−110 | 0.44 |

TABLE IV-continued

Yellow couplers of the formula (400)

R—C—CH—C—NH— [2-Cl, 5-Z phenyl] —NH—C—CH—C—R
       |   ‖                              ‖   |
       X   O                              O   X

| No. | R | Z | X | Melting point °C. | $D_{max}$ |
|-----|---|---|---|------------------|-----------|
| 430 | t-Butyl | $-\overset{O}{\underset{\|}{C}}-N(CH-CH_2-CH_3)_2$<br>$\phantom{-C-N(}CH_3$ | succinimide with gem-dimethyl | 149–151 | 0.45 |
| 431 | t-Butyl | $-\overset{O}{\underset{\|}{C}}-N(CH-CH_2-CH_3)_2$<br>$\phantom{-C-N(}CH_3$ | thiazoline-tosylsulfonylimino | 165–168 | 1.11 |
| 432 | t-Butyl | $-\overset{O}{\underset{\|}{C}}-N(CH=CH_2-CH_3)_2$<br>$\phantom{-C-N(}CH_3$ | 1-benzyl-3-phenylhydantoin | 218–220 | 1.05 |

TABLE V

Yellow couplers of the formula $$R-\underset{\underset{X}{|}}{C}(=O)-CH-\underset{}{C}(=O)-NH-\text{[aryl with }CH_3\text{ (top), }Z\text{ (bottom)]}-NH-C(=O)-CH(X)-C(=O)-R$$

| No. | R | Z | X | Melting point °C. | $D_{max}$ |
|-----|---|---|---|-------------------|-----------|
| 500 | t-Butyl | $-SO_2-NH-(CH_2)_{11}-CH_3$ | (isopropyl-thiadiazolyl)-N=SO_2-C_6H_4-CH_3 | 188–190 | 1.15 |
| 501 | t-Butyl | $-SO_2-NH-(CH_2)_{11}-CH_3$ | (t-butyl-thiadiazolyl)-N=C(=O)-C(CH_3)_3 | 104–107 | 1.22 |

EXAMPLE 8

A solution of 8 g of α-pivaloyl-2-chloro-3-amino-5-[(N,N-di-2-ethylhexylamine)-carbamido]-acetanilide (obtained as in Example 3) and 4.2 g of ethyl p-chlorobenzoylacetate in 300 ml of xylene were reacted in a manner analogous to that in Example 1. The resulting product was crystallised from methanol/water. This gives a product which melts at 62° to 64° C. and is of the following formula:

EXAMPLE 9

The potassium salt of 2-pivaloylamino-5-tert.-butyl-1,3,4-thiadiazole is reacted, in accordance with Example 6, with the coupler of the formula (334).

After separation of the resulting crude product by chromatography, two products in the pure form are obtained, which are of the formulae given below.

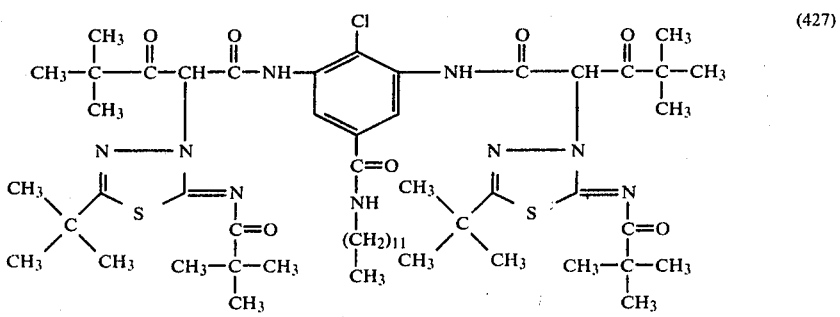

(427)

Melting point: 93°–95° C. and

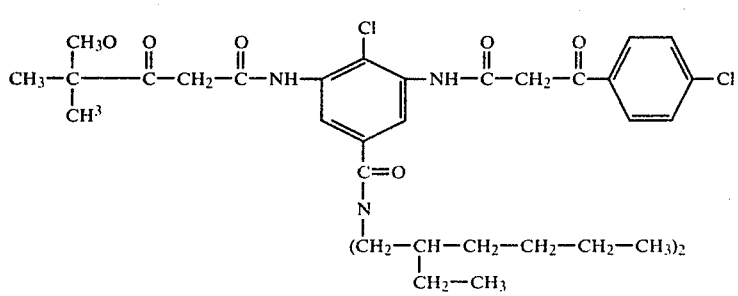

(701)

(702)

[Chemical structure diagram]

Melting point: 104° to 106° C., $D_{max}$ 1.08.

USE EXAMPLES

EXAMPLE 10

Coupler Emulsion 0.05 mmol of the yellow coupler of the formula (402) are dissolved in 2.0 ml of tricresyl phosphate/methylene chloride (1:9). The methylene chloride is evaporated off, 6.6 ml of a 6% strength gelatine solution, 1.2 ml of water and 2.0 ml of an 8% strength aqueous solution of sodium isopropylnaphthalenesulphonate are added, the pH of the mixture is adjusted to a value of 6.5 and the mixture is emulsified for 5 minutes with the aid of an ultrasonic device with an output of 100 watts.

Coating 2.5 ml of the coupler emulsion, freshly exposed to ultrasonic waves, 1.6 ml of silver bromide emulsion which has a pH of 6.5 and contains 1.4% silver and 6.0% of gelatine, 1.0 ml of a 1% strength aqueous solution of the hardener of the formula

[Chemical structure diagram]

and 5.0 ml of water are mixed together and coated, at 40° C., onto a subbed 13 cm×18 cm glass plate.

After the mixture has solidified at 10° C., the plate is dried in a circulating air drying cabinet at room temperature.

Photographic exposure and processing

A strip cut to 4.0 cm×6.5 cm is exposed, at 500 Lux/cm², under a step wedge for 2 seconds and then treated at 24° C. in the following way:

| | Minutes |
|---|---|
| 1. Colour development | 5 |
| 2. Washing | 5 |
| 3. First fixing | 2 |
| 4. Washing | 2 |
| 5. Silver bleaching | 2 |
| 6. Washing | 2 |
| 7. Second fixing | 4 |
| 8. Washing | 10 |
| 9. Drying | 10 |

The processing solutions are of the following composition:

| | |
|---|---|
| I. Colour developing solution (pH = 10.7) | |
| 4-amino-3-methyl-N-ethyl-N-β-(methyl-sulphonamido)-ethyl-aniline; 1½ $H_2SO_4$ × $H_2O$ | 10 mmols |
| anhydrous sodium sulphite | 2.0 g |
| potassium bromide | 0.5 g |
| potassium carbonate | 40.0 g |
| benzyl alcohol | 10.0 g |
| water | to make up to 1,000 ml |
| II. Fixing solution (pH = 4.5) | |
| sodium thiosulphate. 6 $H_2O$ | 80.0 g |
| anhydrous sodium sulphite | 5.0 g |
| sodium borate (Borax) | 6.0 g |
| potassium alum | 7.0 g |
| acetic acid | 4.0 g |
| water | to make up to 1,000 ml |
| III. Silver bleaching bath (pH = 7.2) | |
| potassium ferrycyanide (III) | 100.0 g |
| boric acid | 10.0 g |
| sodium borate (Borax) | 5.0 g |
| water | to make up to 1,000 ml |

A clear, sharp yellow wedge which has an absorption maximum at 443 nm and a colour density of 1.46 is obtained.

Photographic materials can also be produced, and processed, in the same way with the other yellow couplers described in Examples 1 to 9, including the Tables.

For comparison, the following yellow couplers are also employed in a photographic material, which is processed as described above:

the yellow coupler of the formula

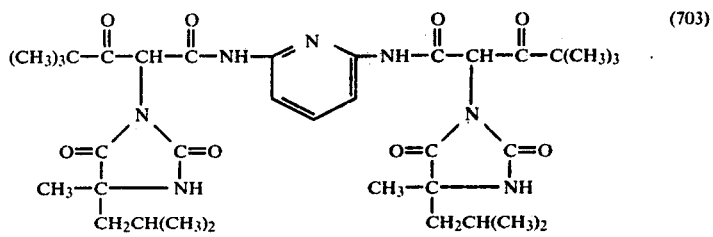

(703)

(Compound No. 50 in German Offenlegungsschrift No. 2,408,168);
the yellow coupler of the formula

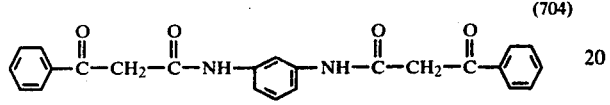

(704)

(U.S. Pat. No. 3,077,403) and

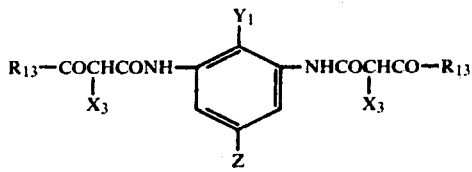

in which $R_{13}$ is straight-chain or branched alkyl having 3 to 10 carbon atoms, cyclopentyl, cyclohexyl, adaman- (705) = (315)

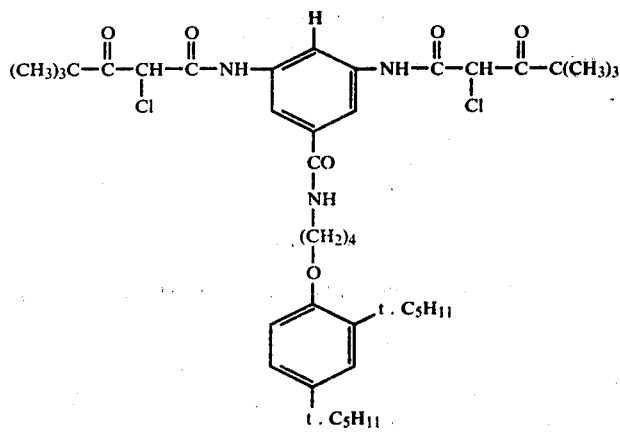

The yellow coupler of the formula (704) is a twice 4-equivalent coupler. Therefore, in the present comparison twice the amount of silver was employed for this coupler.

tyl, phenyl or phenyl substituted by fluorine, chlorine or bromine or alkyl or alkoxy each having 1 to 4 carbon atoms, $X_3$ is hydrogen, chlorine or a radical of the formulae Results

| Compound of the formula | $\lambda_{max}$ [nm] | $D_{max}$ |
|---|---|---|
| (402) | 443 | 1.46 |
| (703) | 440 | 0.11 |
| (704) | 441 | 1.03 |
| (705) | 440 | 0.21 |

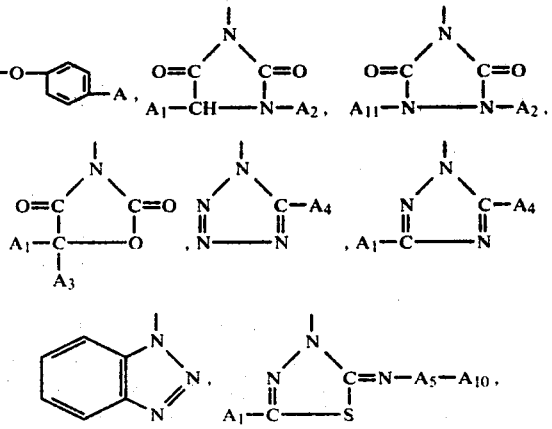

The maximum densities of the yellow dyes which are obtained from the comparison couplers of the formulae (703) to (705) are markedly lower than the corresponding colour density which is obtained using the colour coupler of the formula (402).

What is claimed is:

1. A light sensitive recording material for colour photography which contains in at least one silver halide emulsion layer a yellow coupler of the formula -continued

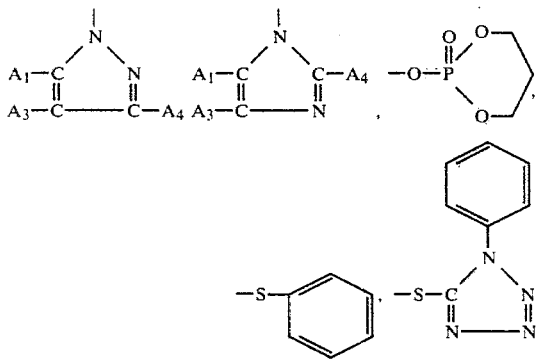

in which A is —COOH, —NO₂, —COOR₁₄, in which R₁₄ is alkyl having 1 to 4 carbon atoms, or the radical of the formula

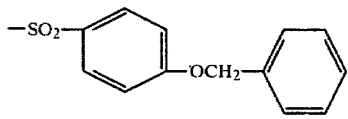

A₁ is hydrogen, alkyl having 1 to 18 carbon atoms, aralkyl, aryl, cycloalkyl having one to four cycloalkyl rings, alkoxy having 1 to 18 carbon atoms, aryloxy, alkylmercapto having 1 to 18 carbon atoms, arylmercapto, halogen, trifluoromethyl, cyano, —NH₂, mono- or a di-alkylamino, in which the alkyl radicals each contain 1 to 18 carbon atoms,

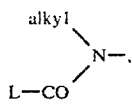

in which alkyl contains 1 to 5 carbon atoms,

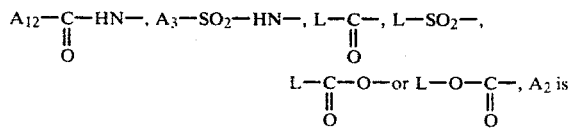

straight-chain or branched alkyl having 1 to 18 carbon atoms, aralkyl, preferably benzyl, or phenyl substituted by alkyl, alkoxy, halogen, —NH₂, alkylamino, dialkylamino, acylamino, —COOH, carbalkoxy, carboxamido, sulphonyl, sulphonamido or alkylmercapto, A₃ is nonbranched or branched alkyl having 1 to 18 carbon atoms which is unsubstituted or substituted by halogen, nitro, cyano, alkoxy or primary, secondary or tertiary amino groups, aralkyl, or cycloalkyl having one to four cycloalkyl rings; aryl which is unsubstituted or substituted by alkyl or alkoxy each having 1 to 4 carbon atoms, halogen, acylamino, —SO₃H, —COOH, sulphonamide or carboxamide, N— or N,N-substituted sulphonamide or carboxamide, carboxylic acid ester, hydroxyl, nitro, primary, secondary or tertiary amine, mercapto, alkylmercapto, —SO₂—L— or —CO—L; pyridyl, furyl, thienyl, perfluoroalkyl, acyl, dialkylamino having, in each case, 1 to 5 carbon atoms in the alkyl part, alkoxy having 1 to 18 carbon atoms or phenoxy, A₄ is hydrogen, substituted or unsubstituted alkyl having 1 to 18 carbon atoms, cycloalkyl, cycloalkenyl, alkenyl, aryl, aralkyl, a heterocyclic radical, alkoxy, aryloxy, alkylmercapto, amino which is unsubstituted or substituted by alkyl, aryl, or acyl, alkylsulphonyl, arylsulphonyl, acyloxy, aminosulphonyl, carboxamide, sulphonamide, alkyl carboxylate, nitro, cyano, halogen, substituted or unsubstituted ureido or substituted or unsubstituted aminosulphonylamino, A₅ is —CO— or —SO₂— and A₁₀ is hydrogen, if A₅ is —CO—, and has the meaning defined for A₃, A₁₁ is alkyl having 1 to 18 carbon atoms which is unsubstituted or substituted by halogen, amino, cyano or alkoxy, cycloalkyl, aryl or aralkyl, A₁₂ is hydrogen and has the meaning defined for A₃ and L is alkyl having 1 to 18 carbon atoms, which is unsubstituted or substituted by halogen, amino, cyano or alkoxy, cycloalkyl, aryl, pyridyl, pyrimidly, furyl or thienyl and Y₁ is fluorine, chlorine, bromine, alkyl, alkoxy and alkylmercapto, each having 1 to 12 carbon atoms, —NH₂, —NHR₁₀, —NR₁₀R₁₁ or —NHCOR₁₂, in which R₁₀ and R₁₁ are alkyl having 1 to 5 carbon atoms or phenyl and R₁₂ is alkyl having 1 to 12 carbon atoms, and Z is alkyl having 5 to 40 carbon atoms, alkoxy having 5 to 40 carbon atoms, cycloalkoxy having 5 to 12 carbon atoms or aralkyl; alkoxyalkyl, alkoxycycloalkyl, cycloalkoxyalkyl, substituted or unsubstituted phenoxyalkyl, alkylamino- and dialkylaminoalkyl, substituted or unsubstituted arylamino- and diarylamino-alkyl, alkylmercaptoalkyl or substituted or unsubstituted arylmercaptoalkyl, in which radicals the sum of the carbon atoms in each case is 6 to 40; or —COOR₃, —COR₃, —NR₃R₄, —CONR₃R₄, —NR₄COR₃, —SO₂R₃, —SO₂NR₃R₄ or —NR₄SO₂R₃, R₃ is substituted or unsubstituted alkyl having 1 to 40 carbon atoms, substituted or unsubstituted cycloalkyl having 5 to 12 carbon atoms or substituted or unsubstituted phenyl and R₄ is hydrogen or alkyl having 1 to 12 carbon atoms.

2. A recording material according to claim 1, wherein Z is alkyl having 5 to 40 carbon atoms, alkoxy having 5 to 40 carbon atoms, cycloalkoxy having 5 to 12 carbon atoms or aralkyl; alkoxyalkyl, alkoxycycloalkyl, cycloalkoxyalkyl, substituted or unsubstituted phenoxyalkyl, alkylamino- and dialkylamino-alkyl, substituted or unsubstituted arylamino- and diarylamino-alkyl, alkylmercaptoalkyl or substituted or unsubstituted arylmercaptoalkyl, in which radicals the sum of the carbon atoms in each case is 6 to 40; or —COOR₃, —COR₃, —NR₃R₄, —CONR₃R₄, —NR₄COR₃, —SO₂R₃₃, —SO₂NR₃₃R₄ or NR₄SO₂R₃₃, in which R₃ is substituted or unsubstituted alkyl having 1 to 20 carbon atoms, substituted or unsubstituted cycloalkyl having 5 to 12 carbon atoms or substituted or unsubstituted phenyl, R₃₃ is alkyl having 1 to 20 carbon atoms or substituted or unsubstituted phenyl and R₄ is hydrogen or alkyl having 1 to 12 carbon atoms.

3. A recording material according to claim 1, wherein Z is alkyl having 5 to 40 carbon atoms; aralkyl; alkoxyalkyl, alkoxycycloalkyl, cycloalkoxyalkyl, substituted or unsubstituted phenoxyalkyl, alkylamino- and dialkylamino-alkyl, substituted or unsubstituted arylamino- and diarylamino-alkyl, alkylmercaptoalkyl or substituted or unsubstituted arylmercaptoalkyl, in which radical the sum of the carbon atoms in each case is 6 to 40; or —COOR₃, —COR₃, —OR₃, —NR₃R₄, —CONR₃R₄, —NR₄COR₃, —SO₂R₃, —SO₂NR₃R₄ or —NR₄SO₂R₃, in which R₃ is straight-chain or branched alkyl having 5 to 40 carbon atoms or cycloalkyl having 5 to 12 carbon atoms and R₄ is hydrogen or straight-chain or branched alkyl having 1 to 12 carbon atoms.

4. A recording material according to claim 1, which contains, as the yellow coupler, a compound of the formula

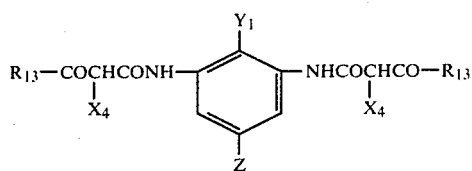

in which X₄ is hydrogen, chlorine or a radical of the formulae

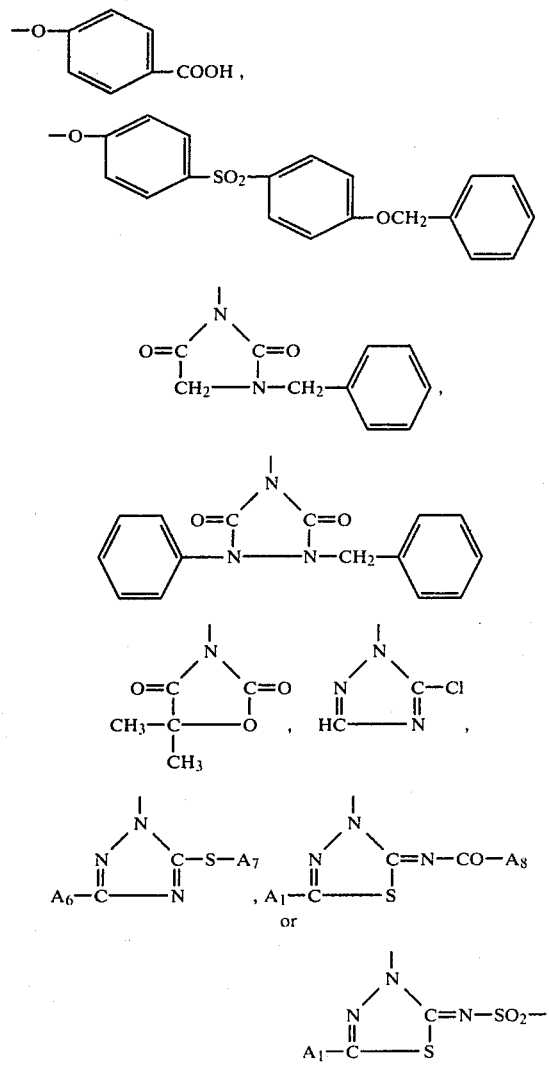

in which A₆ is hydrogen or alkyl having 1 to 4 carbon atoms, A₇ is alkyl having 1 to 12 carbon atoms, A₈ is straight-chain or branched alkyl having 1 to 18 carbon atoms,

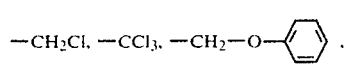

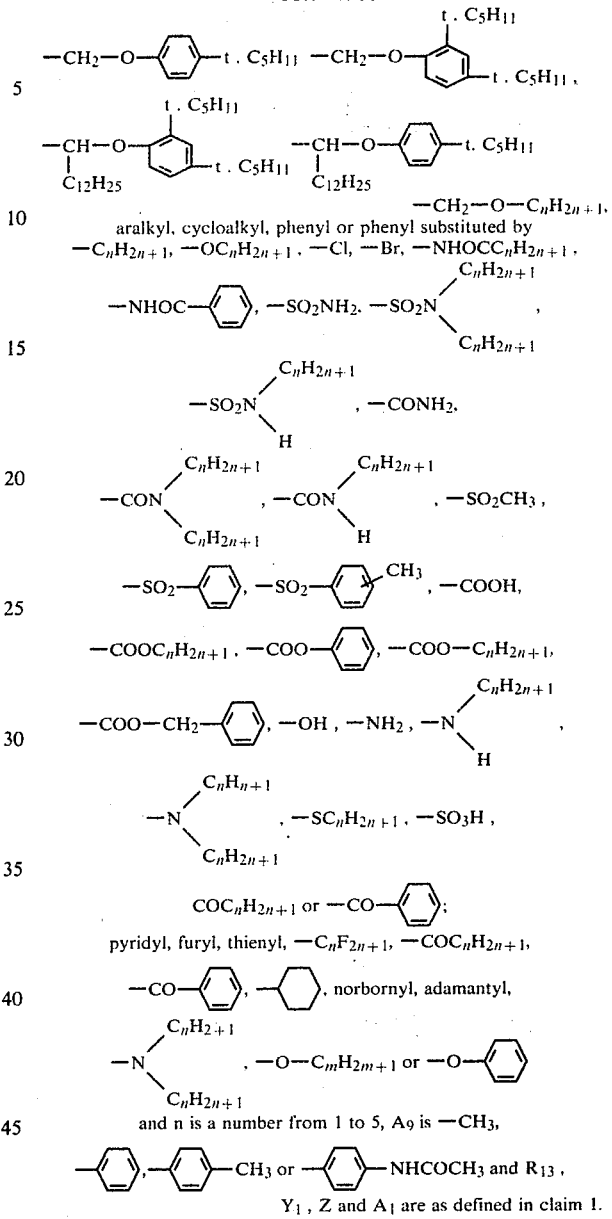

aralkyl, cycloalkyl, phenyl or phenyl substituted by
—$C_nH_{2n+1}$, —$OC_nH_{2n+1}$, —Cl, —Br, —NHOCC$_nH_{2n+1}$, and n is a number from 1 to 5, A₉ is —CH₃, Y₁, Z and A₁ are as defined in claim 1.

5. A recording material according to claim 4, wherein R₁₃ is tert.-alkyl having 4 to 8 carbon atoms.

6. A recording material according to claim 5, wherein R₁₃ is tert.-butyl, 1,1,3,3-tetramethylbutyl, 1-methyl-1-ethyl-pentyl or 1,1-dimethylpropyl.

7. A recording material according to claim 4, wherein Y₁ is chlorine or —NHCOR₁₂, in which R₁₂ is alkyl having 1 to 12 carbon atoms.

8. A recording material according to claim 1, wherein Z is —COOR₃, —CONR₃R₄, —SO₂NR₃R₄ or —NR₄COR₃, in which R₃ is substituted or unsubstituted alkyl having 1 to 40 carbon atoms, substituted or unsubstituted cycloalkyl having 5 to 12 carbon atoms or substituted or unsubstituted phenyl and R₄ is hydrogen or alkyl having 1 to 12 carbon atoms.

9. A recording material according to claim 2, wherein Z is —COOR₃, —CONR₃R₄, —SO₂NR₃₃R₄ or —NR₄COR₃, in which R₃ is substituted or unsubstituted alkyl having 1 to 20 carbon atoms or substituted or unsubstituted cycloalkyl having 5 to 12 carbon atoms or substituted or unsubstituted phenyl, $R_{33}$ is alkyl having 1 to 20 carbon atoms or substituted or unsubstituted phenyl and $R_4$ is hydrogen or alkyl having 1 to 12 carbon atoms.

10. A recording material according to claim 9, wherein Z is —$COOR_3$, —$CONR_3R_4$, —$SO_2NR_{33}R_4$ or —$NR_4COR_3$, in which $R_3$ is alkyl having 1 to 18 carbon atoms,

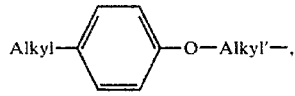

in which alkyl contains 1 to 5 and alkyl' contains 4 to 14 carbon atoms, cyclohexyl, alkylcyclohexyl having 1 to 4 carbon atoms in the alkyl part, phenyl or alkylphenyl having 1 to 5 carbon atoms in the alkyl part, $R_4$ is hydrogen or alkyl having 1 to 8 carbon atoms and $R_{33}$ is as defined in claim 9.

11. A recording material according to claim 3, wherein Z is —$COOR_3$, —$CONR_3R_4$, —$SO_2NR_3R_4$ or —$NR_4COR_3$, in which $R_3$ is straight-chain or branched alkyl having 5 to 40 carbon atoms or cycloalkyl having 5 to 12 carbon atoms and $R_4$ is hydrogen or straight-chain or branched alkyl having 1 to 12 carbon atoms.

12. A recording material according to claim 1, wherein Z is —$COOR_3$, —$CONR_3R_4$, —$SO_2NR_3R_4$ or —$NR_4COR_3$, in which $R_3$ is straight-chain or branched alkyl having 5 to 18 carbon atoms,

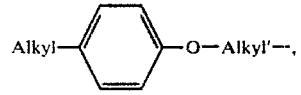

in which alkyl contains 1 to 5 and alkyl' contains 4 to 14 carbon atoms, cyclohexyl, alkylcyclohexyl having 1 to 4 carbon atoms in the alkyl part or alkylphenyl having 1 to 5 carbon atoms in the alkyl part and $R_4$ is hydrogen or alkyl having 1 to 8 carbon atoms.

13. A colour photographic process for the production of a yellow image by colour development of a recording material according to claim 1, which has been exposed image-wise.

* * * * *